United States Patent [19]

Brennan et al.

[11] Patent Number: 4,587,348

[45] Date of Patent: May 6, 1986

[54] PROCESS FOR PREPARING HERBICIDAL 5-CYANO-1-PHENYL-N-METHYL-1H-PYRAZOLE-4-CARBOXAMIDE

[75] Inventors: John Brennan; Eddie V. P. Tao, both of Indianapolis, Ind.

[73] Assignee: Eli Lilly and Company, Indianapolis, Ind.

[21] Appl. No.: 647,569

[22] Filed: Sep. 6, 1984

[51] Int. Cl.$^4$ ............................................. C07D 231/14
[52] U.S. Cl. ................................... 548/378; 548/377
[58] Field of Search ........................................... 548/378

[56] References Cited

U.S. PATENT DOCUMENTS 3,995,044 11/1976 Kabbe et al. ..................... 548/378

OTHER PUBLICATIONS

Cassar, Chem. Abst. 79, 52969y (1973).
Dalton, Chem. Abst. 91, 211047n (1979).
Quan, Chem. Abst. 96, 124512v (1982).

Primary Examiner—Richard A. Schwartz
Assistant Examiner—Kurt G. Briscoe
Attorney, Agent, or Firm—Bruce J. Barclay; Arthur R. Whale

[57] ABSTRACT

The herbicide 5-cyano-1-phenyl-N-methyl-1H-pyrazole-4-carboxamide is prepared in high yield and high purity in a two-step process without isolation of the intermediate.

6 Claims, No Drawings

PROCESS FOR PREPARING HERBICIDAL 5-CYANO-1-PHENYL-N-METHYL-1H-PYRAZOLE-4-CARBOXAMIDE

SUMMARY OF THE INVENTION

The present invention provides a process for preparing 5-cyano-1-phenyl-N-methyl-1H-pyrazole-4-carboxamide of the formula

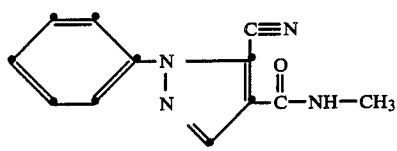

comprising the following steps:

a. reacting a 5-chloro-1-phenyl-1H-pyrazole-4-carboxylic acid ester of the formula

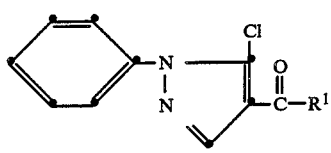

wherein $R^1$ is $C_1-C_6$ alkoxy, with from about 2.0 to about 3.0 mole equivalents of sodium cyanide in from about 600 ml to about 1 l. of a suitable solvent per gram-mole of the 5-chloro-1-phenyl-1H-pyrazole-4-carboxylic acid ester at a temperature in the range of about 70° C. to about 150° C.; and b. adding from about 2.0 to about 15.0 mole equivalents of methylamine to the reaction mixture, stirring the mixture at a temperature in the range of about 20° C. to about 40° C. and separating the final product.

DETAILED DESCRIPTION OF THE INVENTION

All temperatures stated herein are in degrees Celsius. All quantities herein specified are in weight units, except for liquids, which are in volume units.

The term $C_1-C_6$ alkoxy represents a straight or branched alkoxy chain having from one to six carbon atoms. Typical $C_1-C_6$ alkoxy groups include methoxy, ethoxy, n-propoxy, sec.-butoxy, neopentoxy, n-hexoxy and the like. Of these, ethoxy is preferred.

In the first step of the process of the present invention, a 5-chloro-1-phenyl-1H-pyrazole-4-carboxylic acid ester is treated with sodium cyanide in a suitable solvent to afford the corresponding 5-cyano derivative. This step of the process is preferably carried out in the presence of at least approximately 2.0 mole equivalents of sodium cyanide, but quantities as great as 3.0 mole equivalents have been found to provide the desired product as well. Quantities greater than about 3.0 mole equivalents of sodium cyanide have been found to be detrimental to the present process.

Suitable solvents for use in the present process include most of the polar, aprotic solvents such as N,N-dimethylacetamide (DMAC), dimethylsulfoxide (DMSO), and preferably N,N-dimethylformamide (DMF). As in any chemical process, the concentration of reactants in the reaction mixture is not critical, but it is preferred to employ the least amount of solvent necessary to keep the reactants in solution. The range of practical concentrations depends in part on the power of the mixing equipment used, and in part on the solubility of the reactants in the chosen solvent. Generally, it is convenient to conduct the reaction at a concentration in the range of about 600 ml to about 1 l. of a suitable solvent per gram-mole of 5-chloropyrazole starting material, with about 600 ml of solvent per gram-mole being preferred. This concentration range is both economical and convenient in large-scale production. Higher concentrations of the reactants are feasible with the understanding that it will not be possible to carry out the desired smooth conversion of reactants from step to step if the intermediate product is allowed to partially precipitate out of solution.

The first step of the present process is substantially complete after about 6 to 24 hours or more when conducted at a temperature in the range of about 70° C. to about 150° C. The reaction is preferably conducted for about 6 hours at about 100° C.

When the first step of the reaction is complete, the mixture is allowed to cool to a temperature in the range of about 20° C. to about 30° C. The reaction mixture is then typically stirred at that temperature until used in the second step of the present process. Another advantage of the present process is that it is not necessary to either isolate the intermediate 5-cyano-1-phenyl-1H-pyrazole-4-carboxylic acid ester formed by the first step of the present process or purify it in any manner.

The second step of the present process relates to the conversion of the intermediate 5-cyano-1-phenyl-1H-pyrazole-4-carboxylic acid ester derivative to the corresponding amide herbicide by reaction with methylamine. This step of the process is carried out by adding methylamine to the stirring reaction mixture containing the 5-cyano-1-phenyl-1H-pyrazole-4-carboxylic acid ester prepared in step one above. The methylamine employed in the present process may be either bubbled subsurface into the reaction mixture in gaseous form, preferably under a sealed reaction vessel, or preferably added to the reaction mixture as an aqueous solution. It is preferred to use at least approximately 2.0 mole equivalents of amine for each mole of 5-cyanopyrazole starting material present in the reaction mixture. Greater quantities of amine may be employed if desired, for example, up to about 15.0 mole equivalents of amine for each mole of starting material, but this is not economically advantageous. The particularly preferred amount of methylamine employed in this step of the process is 3.5 mole equivalents. Further, if aqueous methylamine is employed, the pyrazole derivatives prepared herein are water insoluble and may begin to precipitate if too much water is present in the reaction mixture.

The second step of the process of the invention is carried out at a temperature in the range of about 20° C. to about 40° C., preferably at about 25° C. or typically the room temperature where the reaction is carried out. The reaction is conducted until the final product is formed, which generally takes from about 3 to 24 hours or more, preferably about 6 hours.

The herbicidal pyrazole product is easily isolated if desired by simply adding water to the reaction mixture and collecting the solid precipitate, preferably by vacuum filtration. The product thus isolated is generally washed with water, vacuum dried and is suitable for use as a herbicidal agent.

The process of the present invention is particularly advantageous because it is capable of preparing the valuable herbicide which is its product in high purity without additional purification, and without the isolation of the intermediate which is formed. Further, the process may be carried out under simplified conditions in an inexpensive manner, and as such the process is particularly well suited for the large-scale industrial synthesis of the pyrazole herbicide. Further, since the process can be conducted without isolation of the intermediate, the reaction is especially safe to perform since operator exposure to the chemical reagents is minimal.

Yet another advantage of the present process is the absence of expensive or laborious procedures for purifying the final product. This is especially important when using the present process in a large-scale operation. The filtered product obtained above typically has a purity in the range of about 95% to about 100%. While additional purification is not necessary nor preferred, it may be conducted if desired by routine procedures such as recrystallization from common solvents or purification over solid supports such as silica gel or alumina. The present process has been found to typically provide the final product in a yield between 80% and 87% when employing starting 5-chloropyrazole which is substantially free from impurities.

The compound prepared by the process of the present invention is useful both as a preemergent and postemergent herbicide. This compound is used for controlling undesired plants by applying it to the plants, or to the locus of the plants, in a growth inhibiting amount.

The term "growth inhibiting amount", as defined herein, refers to an amount of the compound which either kills or stunts the growth of the weed species for which control is desired. This amount will generally be from about 0.05 to about 20.0 pounds or greater of the compound per acre (about 0.056 to about 22.4 kg/ha). The compound is more preferably applied at rates of about 0.10 to about 8.0 pounds per acre (about 0.112 to about 8.96 kg/ha). The exact concentration of active ingredient required varies with the weed species to be controlled, type of formulation, soil type, climate conditions and the like.

The term "undesired plants", as defined herein, refers to both weeds and weed seeds which are present at the location to be treated with the compound. This compound can be applied to the soil to selectively control undesired plants by soil contact when the weed seeds are germinating and emerging. It can also be used directly to kill emerged weeds by direct contact with the exposed portion of the weed.

The compound synthesized by the present process is preferably formulated with a suitable agriculturally-acceptable carrier for ease of application. Such compositions will contain from about 0.1 to about 95.0 percent by weight of the active ingredient, depending on the composition desired. Examples of typical herbicidal compositions contemplated include sprayable formulations, such as wettable powders, aqueous suspensions and emulsifiable concentrates; and solid compositions, such as dusts and granules.

The starting materials employed in the present process are prepared by prior art procedures or by processes analogous to such prior art procedures. The preferred process for preparing the 5-chloro-1-phenyl-1H-pyrazole-4-carboxylic acid ester involves reacting phenylhydrazine with an alkyl (alkoxymethylene)cyanoacetate to provide the corresponding 5-amino-1-phenyl-1H-pyrazole-4-carboxylic acid ester which is then reacted with an appropriate halogenating agent to afford the corresponding 5-chloropyrazole starting material. This reaction is represented by the following scheme:

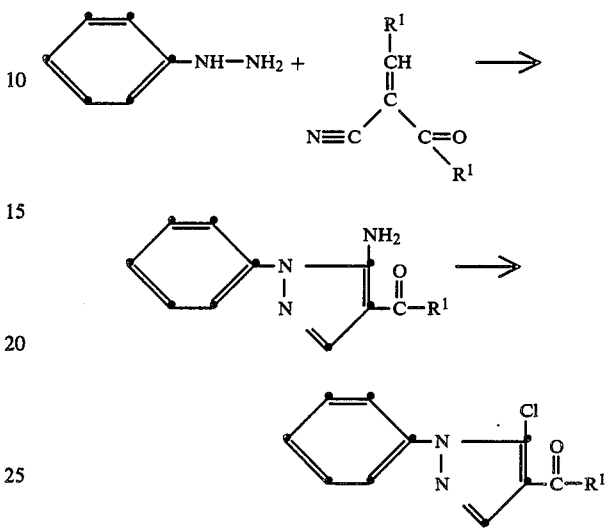

wherein each $R^1$ may be the same or different and is as defined above.

The reaction of phenylhydrazine with an alkyl (alkoxymethylene)cyanoacetate to prepare a 5-amino-4-pyrazolecarboxylic acid ester is readily practiced by well known procedures. Typically, equimolar quantities of the two starting materials are combined in a mutual solvent, such as methanol or ethanol. The mixture is stirred at a temperature in the range of from about 20° C. to 200° C., more preferably at reflux temperature of the reaction mixture. The product thus formed after about 2 to 24 hours is then isolated and purified according to standard procedures.

The 5-chloro-4-pyrazolecarboxylic acid esters used as starting materials in the present process are prepared by employing nitrosyl chloride as both a diazotizing and halogenating agent. This reaction is typically performed in a non-reactive organic solvent and preferably in the presence of an acid catalyst. Typical solvents include most halogenated solvents with chloroform and carbon tetrachloride being preferred. An excess of the nitrosyl chloride is typically bubbled into the reaction mixture for about 5 to 30 minutes. The mixture can then be heated on a steam bath for a short period of time. The product is then isolated by simply removing the volatiles under reduced pressure and purifying the product by common techniques if desired.

The following Examples further illustrate specific aspects of the present invention. The Examples are not intended to be limiting to the scope of the process of the present invention in any respect and should not be so construed.

The following conditions were employed for all high pressure liquid chromatogrphy data listed below. The column employed was a Zorbex C-8 column having the dimensions 25 cm×4.6 mm I.D. The eluent was composed of 60 parts HPLC grade water, 10 parts methanol and 30 parts UV grade tetrahydrofuran. The flow rate was two ml/minute. Detection was at 254 nanometers.

The sample was injected at 10–15 μl from a sample of 200–400 μg/ml in methanol.

EXAMPLE 1

A 250 ml round bottom flask fitted with a mechanical stirrer was charged with 25.0 g (0.1 mol) of 92.33% pure 5-chloro-1-phenyl-1H-pyrazole-4-carboxylic acid, ethyl ester and 60 ml of DMF. The mixture was stirred at room temperature for a short period and then 9.8 g (0.2 mol) of sodium cyanide was added. The resulting dark mixture was heated at approximately 100° C. for 6 hours and cooled to room temperature. The reaction mixture was stirred for approximately 12 hours at this temperature and then charged with 27.13 g (0.35 mol) of an aqueous solution of 40% methylamine by weight (hereinafter 40% aqueous methylamine, from Aldrich Chemical Co., Milwaukee Wis.). The reaction mixture was stirred for approximately 6½ hours and 60 ml of water was added. The resulting suspension was stirred for approximately 10 minutes and the precipitated solid was collected by filtration. The solid was washed with water and vacuum dried to provide 18.36 g of 5-cyano-1-phenyl-N-methyl-1H-pyrazole-4-carboxamide. A high pressure liquid chromatographic analysis of the final product indicated it to be 97.86% pure. Corrected yield 86.1%. m/e 226.

Analysis calculated for $C_{12}H_{10}N_4O$: Theory: C, 63.71; H, 4.46; N, 24.76; Found: C, 64.01; H, 4.20; N, 24.54.

EXAMPLE 2

A mixture of 25.4 g (0.1 mol) of 96.17% pure 5-chloro-1-phenyl-4-carboxylic acid, ethyl ester, 9.8 g (0.2 mol) of sodium cyanide and 75 ml of DMF was heated at 100° C. for 6 hours. The reaction mixture was stirred at room temperature for approximately 17 hours and 27.13 g (0.35 mol) of 40% aqueous methylamine was added dropwise to reaction mixture over a period of approximately 5 minutes. The reaction mixture was stirred at room temperature for approximately 22 hours and 75 ml of water was added. The mixture was stirred for approximately one additional hour and the precipitated solid was collected by filtration. The collected solid was vacuum dried to provide 19.4 g of 5-cyano-1-phenyl-N-methyl-1H-pyrazole-4-carboxamide. Purity by HPLC was 98.5% and the corrected yield was 87.9% product.

EXAMPLE 3

A 250 ml round bottom flask fitted with a mechanical stirrer was charged with 25.4 g (0.1 mol) of 96.17% pure 5-chloro-1-phenyl-1H-pyrazole-4-carboxylic acid, ethyl ester, 9.8 g (0.2 mol) of sodium cyanide and 100 ml of DMF. The reaction mixture was stirred at room temperature, and then heated to approximately 100° C. and stirred for 6 hours. The reaction mixture was cooled to room temperature and stirred for approximately 12 hours. A solution of 40% aqueous methylamine (27.13 g, 0.35 mol) was added dropwise to the reaction mixture. The reaction mixture was stirred for approximately 22 hours and 100 ml of water was added. The precipitated solid was collected by filtration and vacuum dried to afford 18.84 g of 5-cyano-1-phenyl-N-methyl-1H-pyrazole-4-carboxamide. HPLC indicated 99.35% pure product and the corrected yield of the product was 86.1%.

EXAMPLE 4

Four and seven tenths grams (0.096 mol) of sodium cyanide were added to a solution of 12.0 g (0.048 mol) of 94.66% pure 5-chloro-1-phenyl-1H-pyrazole-4-carboxylic acid, ethyl ester in 28.8 ml of DMF at room temperature. The solution was heated for 6 hours at 100° C. and cooled to room temperature. The reaction mixture was stirred overnight and 13.0 g (0.17 mol) of 40% aqueous methylamine was added dropwise. The resulting mixture was stirred for 6 hours at room temperature and 28.8 ml of water was slowly added. The mixture was stirred for 10 minutes and the precipitated solid was collected by filtration. This solid was washed with water and vacuum dried to provide 8.3 g of 5-cyano-1-phenyl-N-methyl-1H-pyrazole-4-carboxamide as a white solid. The product analyzed 95.81% pure by high pressure liquid chromatography, corresponding to a corrected yield of 77.4% product.

EXAMPLE 5

A 250 ml round bottom flask was charged with 25.4 g (0.1 mol) of 96.17% pure 5-chloro-1-phenyl-1H-pyrazole-4-carboxylic acid, ethyl ester, 9.8 g (0.2 mol) of sodium cyanide and 100 ml of DMF. The resulting mixture was heated at 100° C. for 6 hours and cooled to room temperature. The mixture was stirred overnight for approximately 12 hours and 27.16 g (0.35 mol) of 40% aqueous methylamine was added dropwise. The resulting reaction mixture was stirred for 22 hours and 100 ml of water was added thereto. The precipitated solid was collected by filtration and vacuum dried to obtain 18.84 g of the desired product which analyzed 99.35% pure by high pressure liquid chromatography, corresponding to a corrected yield of 86.1%.

EXAMPLE 6

A 100 ml 3-neck round bottom flask was charged with 12.0 g (0.048 mol) of 99.1% pure 5-chloro-1-phenyl-1H-pyrazole-4-carboxylic acid, ethyl ester, 4.7 g (0.096 mol) of sodium cyanide and 28.8 ml of DMF. The resulting mixture was heated at approximately 100° C. for 6 hours and then stirred at room temperature overnight. Thirteen grams (0.17 mol) of 40% aqueous methylamine were added to the reaction mixture dropwise. The reaction mixture was stirred at room temperature for 6½ hours and 28.8 ml of water was added. The mixture was stirred for 30 minutes and the precipitated solid was collected by filtration. The resulting solid was washed with water and vacuum dried to afford 9.2 g of 5-cyano-1-phenyl-N-methyl-1H-pyrazole-4-carboxamide. The corrected yield was 73.4% and purity of the final product by high pressure liquid chromatography was 85.8%.

EXAMPLE 7

A mixture of 25.4 g (0.1 mol) of 96.17% pure 5-chloro-1-phenyl-1H-pyrazole-4-carboxylic acid, ethyl ester, 9.8 g (0.2 mol) of sodium cyanide and 75 ml of DMF was heated at 100° C. for 6 hours. The mixture was cooled and stirred for 17 hours at room temperature. A solution of 27.13 g (0.35 mol) of 40% aqueous methylamine was added dropwise to the reaction mixture over a 5 minute period, and the resulting mixture was stirred at room temperature for 22 hours. Seventy-five milliliters of water were added and the reaction mixture was stirred at room temperature for approximately 1 hour. The precipitate was collected by filtration and vacuum dried to afford 19.4 g of 5-cyano-1-phenyl-N-methy-1H-pyrazole-4-carboxamide. Purity of this material as determined by high pressure liquid chromatography was 98.5%. The corrected yield of the product was 87.9%.

The following Example demonstrates the advantages obtained by the present process when employed on a large scale.

EXAMPLE 8

A 50 gallon reactor was charged with 16.6 kg (66.3 mol) of 5-chloro-1-phenyl-1H-pyrazole-4-carboxylic acid, ethyl ester and 40 l. of DMF. To the stirred solution was added 6.5 kg (132.6 mol) of sodium cyanide and the resulting reaction mixture was heated at 85° C. for 5 hours. The mixture was allowed to stir overnight at room temperature. A thin layer chromatograph in methylene chloride of a sample of the reaction mixture indicated the presence of a small amount of starting material. the reaction mixture was heated to 100° C. for 2 hours and cooled. The mixture was charged with 18 kg (232 mol) of 40% aqueous methylamine. The mixture was stirred at room temperature overnight and 40 l. of ice water was added. The mixture was stirred at about 10° C. for one hour using a cooling jacket and the precipitated solid was collected by filtration. The solid was washed with water several times and dried to provide 12.4 kg of 5-cyano-1-phenyl-N-methyl-1H-pyrazole-4-carboxamide. Yield 82.7%. Purity of this material by HPLC was 98.14%. mp=203°–205° C.

Analysis calculated for $C_{12}H_{10}N_4O$: Theory: C, 63.71; H, 4.46; N, 24.76; Found : C, 63.62; H, 4.21; N, 24.50.

While it is preferred to use DMF as the solvent in the present process, the following two examples illustrate the use of the present process with solvents other than DMF.

EXAMPLE 9

A 500 ml 3-neck round bottom flask fitted with a mechanical stirrer was sequentially charged with 40.0 g (0.16 mol) of 5-chloro-1-phenyl-1H-pyrazole-4-carboxylic acid, ethyl ester, 15.68 g (0.32 mol) of sodium cyanide and 96 ml of N,N-dimethylacetamide. The mixture was heated at approximately 100° C. for about 6 hours, cooled and stirred at room temperature overnight. Next, 43.4 g (0.56 mol) of 40% aqueous methylamine was added to the mixture, which was stirred at room temperature for 6½ hours. Water (96 ml) was added to the reaction mixture dropwise and the mixture was stirred for about one hour. The precipitated solid was collected by filtration, and the solid was washed with water and vacuum dried to provide 29.85 g of product. The solid was 88.22% pure product to afford a corrected yield of 73.3%.

EXAMPLE 10

A 500 ml 3-neck round bottom flask fitted with a mechanical stirrer was sequentially charged with 40.0 g (0.16 mol) of 5-chloro-1-phenyl-1H-pyrazole-4-carboxylic acid, ethyl ester, 15.68 g (0.32 mol) of sodium cyanide and 96 ml of dimethylsulfoxide. The reaction mixture was heated to about 125° C. and cooled to 100° C., at which temperature the reaction mixture was stirred for 6 hours. The mixture was stirred at room temperature overnight and charged with 43.4 g (0.56 mol) of 40% queous methylamine dropwise. The resulting mixture was stirred for 6½ hours at room temperature and 96 ml of water was added thereto. The mixture was stirred for one hour and the precipitated solid was collected by vacuum filtration. The resulting solid was washed with water and vacuum dried to afford 27.5 g of 96.19% pure 5-cyano-1-phenyl-N-methyl-1H-pyrazole-4-carboxamide. Corrected yield 73.6%.

We claim:

1. A process for preparing 5-cyano-1-phenyl-N-methyl-1H-pyrazole-4-carboxamide of the formula

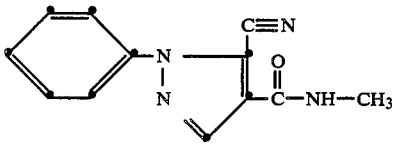

comprising the following steps:
a. reacting a 5-chloro-1-phenyl-1H-pyrazole-4-carboxylic acid ester of the formula

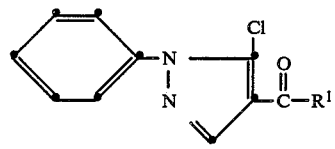

wherein $R^1$ is $C_1$–$C_6$ alkoxy, with from about 2.0 to about 3.0 mole equivalents of sodium cyanide in from about 600 ml to about 1 l. of a suitable solvent per gram-mole of the 5-chloro-1-phenyl-1H-pyrazole-4-carboxylic acid ester at a temperture in the range of about 70° C. to about 150° C.; and
b. adding from about 2.0 to about 15.0 mole equivalents of methylamine to the reaction mixture, stirring the mixture at a temperature in the range of about 20° C. to about 40° C. and separating the final product.

2. A process of claim 1 wherein $R^1$ is ethoxy.

3. A process of claim 2 wherein about 2.0 mole equivalents of sodium cyanide are employed.

4. A process of claim 2 wherein about 600 ml of suitable solvent per gram-mole of 5-chloro-1-phenyl-1H-pyrazole-4-carboxylic acid ester is employed.

5. A process of claim 2 wherein the suitable solvent is N,N-dimethylformamide.

6. A process of claim 2 wherein about 3.5 mole equivalents of methylamine are employed.

* * * * *